(12) United States Patent
Willmitzer et al.

(10) Patent No.: US 6,215,042 B1
(45) Date of Patent: Apr. 10, 2001

(54) PLASMIDS CONTAINING DNA-SEQUENCES THAT CAUSE CHANGES IN THE CARBOHYDRATE CONCENTRATION AND CARBOHYDRATE COMPOSITION IN PLANTS, AS WELL AS PLANT CELLS AND PLANTS CONTAINING THESE PLASMIDS

(75) Inventors: Lothar Willmitzer; Uwe Sonnewald; Jens Kossmann; Bernd Müller-Röber, all of Berlin (DE); Richard G. F. Visser, Bennekom; Evert Jacobsen, Wageningen, both of (NL)

(73) Assignee: Hoeschst Schering Agrevo GmbH, Berlin (DE)

( * ) Notice: Subject to any disclaimer, the term of this patent is extended or adjusted under 35 U.S.C. 154(b) by 0 days.

(21) Appl. No.: 08/104,158

(22) PCT Filed: Feb. 11, 1992

(86) PCT No.: PCT/EP92/00302

§ 371 Date: Aug. 13, 1993

§ 102(e) Date: Aug. 13, 1993

(87) PCT Pub. No.: WO92/14827

PCT Pub. Date: Sep. 3, 1992

(30) Foreign Application Priority Data

Feb. 13, 1991 (DE) .................................. 41 04 782
Feb. 11, 1992 (WO) .................................. PCT/EP92/00302

(51) Int. Cl.[7] .............................. A01H 5/00; C12N 5/04; C12N 15/82
(52) U.S. Cl. ...................... 800/284; 800/298; 800/317.2; 435/419; 435/417; 435/468; 536/23.6
(58) Field of Search .......................... 800/205, DIG. 55, 800/DIG. 56, DIG. 57, DIG. 58, DIG. 23, DIG. 26, DIG. 52, DIG. 15, DIG. 40, DIG. 42, DIG. 43, DIG. 44, 284, 298, 312, 317.2, 317.3, 317.4, 320, 320.1, 320.3; 435/172.3, 320.1, 419, 468, 417, 69.1; 536/23.6, 23.1, 24.1

(56) References Cited

U.S. PATENT DOCUMENTS 4,723,052 * 2/1988 Cochran ............................ 800/200

FOREIGN PATENT DOCUMENTS

0368506 * 5/1990 (EP) .............................. C12N/15/54
0455316   11/1991 (EP) .
8912386   12/1989 (WO) .
9012084   10/1990 (WO) .
9012876   11/1990 (WO) .

OTHER PUBLICATIONS

Smith et al. (1988) Nature 334: 724–726.*
Goodwin et al (eds.) (1985) Introduction to Plant Biochemistry, pp. 253–261, Pergamon Press, Oxford.*
Rosahl et al. (1986) Mol Gen Genet 202: 368–373.*
Vos Scheperkeuter et al (1989) Plant Physiol 90: 75–84.*
Twell et al (1987) Plant Mol Biol 9: 345–375.*
Nepoli et al (1990) The Plant Cell 2: 279–289.*
Bhattacharyya, M.K., et al; "The Wrinkled–Seed Character of Pea Described by Mendel is Caused by a Transposon–Like Insertion in a Gene Encoding Starch–Branching Enzyme"; Cell, vol. 60, Jan. 12, 1990, pp. 115–122.
Visser, R.G.F., et al; "Manipulation of Starch in Potatoes by New Mutants and Antisense RNA"; J. Cell. Biochem. Suppl., vol. 14E, 1990, pp. 271.
Visser, R.G.F., et al; "Inhibition of the Expression of the Gene For Granule–Bound Starch Synthase in Potato by Antisense Constructs"; Mol. Gen. Genet., vol. 225, No. 2, Feb. 1991, pp. 289–296.
Dilworth, M.F.; "Molecular Biology Comes Home"; The Plant Cell, vol. 3, No. 3, 1991, Rockville, MD, pp. 213–218; See p. 216, right column, last paragraph–p. 217, left column and Oral Disclosure by L. Willmitzer, Keystone Symposium, held Jan. 10–17, 1991.
Van Der Leij, F.R., et al; "Expression of the Gene Encoding Granule Bound Starch Synthase After Introduction in an Amylose–Free and a Wildtype Potato (*Solanum tuberosum*)"; Abstracts VIITH International Congress on Plant Tissue Culture and Cell Culture, Abstract A5–36 1990, Amsterdam, Jun. 24–29, 1990, pp. 177.
Kossmann, J., et al; "Cloning and Expression Analysis of a Potato cDNA That Encodes Branching Enzyme: Evidence for Co–Expression of Starch Biosynthetic Genes"; Mol. Gen. Genet. vol. 230, No. 1–2, Nov. 1991, pp. 39–44.

* cited by examiner

Primary Examiner—Elizabeth F. McElwain
(74) Attorney, Agent, or Firm—Frommer Lawrence Haug&LLP

(57) ABSTRACT

Plasmids are described having DNA sequences that after insertion into the genome of the plants cause changes in the carbohydrate concentration and the carbohydrate composition in regenerated plants. These changes can be obtained from a sequence of a branching enzyme that is located on these plasmids. This branching enzyme alters the amylose/amylopectin ratio in starch of the plants, especially in commercially used plants.

21 Claims, 5 Drawing Sheets

Plasmid p33 - BE   14,6 kb

Plasmid p33 - anti - BE    14,6 kb

PLASMIDS CONTAINING DNA-SEQUENCES THAT CAUSE CHANGES IN THE CARBOHYDRATE CONCENTRATION AND CARBOHYDRATE COMPOSITION IN PLANTS, AS WELL AS PLANT CELLS AND PLANTS CONTAINING THESE PLASMIDS

This application is a national stage application of PCT/EP92/00302 filed Feb. 11, 1992.

The present invention relates to plasmids containing DNA-sequences which contain information that, after insertion into a plant genome, cause changes in the carbohydrate concentration and the carbohydrate composition in regenerated plants, as well as plant cells and plants containing sequences from these plasmids.

Because of the continual growth in the world population, there is a continually growing demand for nutrient and raw materials. It is the task of biotechnological research to achieve a change in the content as well as the yield of crops. To do this the metabolism of plants has to be altered.

Of particular interest is the possibility of using plant ingredients as renewable sources of raw material sources e.g. for the chemical industry. Renewable sources are of great importance for two reasons. Firstly, up to now, mineral oil and coal deposits have been the main source of raw materials for the petrochemical industry. Such deposits are finite, however, so that alternative, renewable raw material sources must be developed.

Secondly, the present situation of agriculture in Europe and North America has lead to a surplus of crops grown for their nutritive properties. This causes obvious financial and political problems in agriculture. Alternative products for which there is a higher quantitative demand could be a solution to this problem.

Renewable raw materials can be divided into fats and oils, proteins and carbohydrates, such as mono-, di-, oligo- and polysaccharides. The most important polysaccharides are starch and cellulose. In the EEC, the total starch production in 1987–1988 comprised maize (60%), wheat (19%) and potato (21%).

For an increasing use of plant starch as an industrial raw material the quality of the starch must meet the demands of the processing industry. Important considerations include the amylose to amylopectin ratio, the chain length, the branching grade of the amylopectin as well as the size of the starch granules.

The main biochemical synthetic pathways for the production of starch in higher plants are well known. Starch consists of amylose and amylopectin, in which the amylose consists of a linear $\alpha$-1,4-glucan and amylopectin consists of $\alpha$-1,4-glucans, which are connected to each other via $\alpha$1,6-linkages and thus form a branched polyglucan. The so-called branching enzyme (Q-enzyme) is responsible for the introduction of the $\alpha$-1,6-linkage. One method for the production of starch which only has a linear $\alpha$-1,4-glucan structure is therefore by the inhibition of the enzymatic activity of the proteins and/or the inhibition of the biosynthesis of the branching enzyme. New biotechnology processes for the genetic alteration of dicotyledonous and monocotyledonous plants by transfer and stable installation of single isolated genes or groups of genes are known (Gasser and Fraley Science 244 1293–1299). The possibility of specific expression of foreign genes inserted in the plant by gene technology, primarily in potato tubers, is also known (EP 375092 and Rocha-Sosa et al., EMBO J. 8, 23–29 (1989)).

The present invention provides plasmids containing DNA-sequences which contain information that, after insertion into a plant genome, cause changes in the carbohydrate concentration and the carbohydrate composition in regenerated plants.

The invention further provides plant cells containing sequences from these plasmids which can be regenerated to whole plants, as well as plants containing sequences from these plasmids.

The term "plant" means a commercially useful plant, preferably maize, barley, wheat, rice, peas, soya beans, sugar cane, sugar beet, tomato, potato or tobacco.

Carbohydrates which can be altered by the DNA sequences are mono-, di-, oligo- or polysaccharides. Starch is an example of a polysaccharide which can be modified in plants and plant cells.

With the plasmids of the invention, it is possible to modify the amylose to amylopectin ratio of the starch in plant cells and in plants. This is possible through the presence of a branching enzyme, located on the plasmid, which has the following sequence: identified as SEQ ID NO:1

```
            10        20        30        40        50        60
  1 TCAGGAGCGGTCTTGGGATATTTCTTCCACCCCAAAATCAAGAGTTAGAAAAGATGAAAG

61 GATGAAGCACAGTTCAGCTATTTCCGCTGTTTTGACCGATGACAATTCGACAATGGCACC

121 CCTAGAGGAAGATGTCAACACTGAAAATATTGGCCTCCTAAATTTGGATCCAACTTTGGA

181 ACCTTATCTAGATCACTTCAGACACAGAATGAAGAGATATGTGGATCAGAAAATGCTCAT

241 TGAAAAATATGAGGGACCCCTTGAGGAATTTGCTCAAGGTTATTTAAAATTTGGATTCAA

301 CAGGGAAGATGGTTGCATAGTCTATCGTGAATGGGCTCCTGCTGCTCAGGAAGCAGAAGT

361 TATTGGCGATTTCAATGGTAGGAACGGTTCTAACCACATGATGGAGAAGGACCAGTTTGG

421 TGTTTGGAGTATTAGAATTCCTGATGTTGACAGTAAGCCAGTCATTCCACACAACTCCAG

481 AGTTAAGTTTCGTTTCAAACATGGTAATGGAGTGTGGGTAGATCGTATCCCTGCTTGGAT

541 AAAGTATGCCACTGCAGACGCCACAAAGTTTGCAGCACCATATGATGGTGTCTACTGGGA

601 CCCACCACCTTCAGAAAGGTACCACTTCAAATACCCTCGCCCTCCCAAACCCCGAGCCCC
```

-continued

```
 661 ACGAATCTACGAAGCACATGTCGGCATGAGCAGCTCTGAGCCACGTGTAAATTCGTATCG
 721 TGAGTTTGCAGATGATGTTTTACCTCGGATTAAGGCAAATAACTATAATACTGTCCAGTT
 781 GATGGCCATAATGGAACATTCTTACTATGGATCATTTGGATATCATGTTACAAACTTTTT
 841 TGCTGTGAGCAATAGATATGGAAACCCGGAGGACCTAAAGTATCTGATAGATAAAGCACA
 901 TAGCTTGGGTTTACAGGTTCTGGTGGATGTAGTTCACAGTCATGCAAGCAATAATGTCAC
 961 TGATGGCCTCAATGGCTTTGATATTGGCCAAGGTTCTCAAGAATCCTACTTTCATGCTGG
1021 AGAGCGAGGGTACCATAAGTTGTGGGATAGCAGGCTGTTCAACTATGCCAATTGGGAGGT
1081 TCTTCGTTTCCTTCTTTCCAACTTGAGGTGGTGGCTAGAAGAGTATAACTTTGACGGATT
1141 TCGATTTGATGGAATAACTTCTATGCTGTATGTTCATCATGGAATCAATATGGGATTTAC
1201 AGGAAACTATAATGAGTATTTCAGCGAGGCTACAGATGTTGATGCTGTGGTCTATTTAAT
1261 GTTGGCCAATAATCTGATTCACAAGATTTTCCCAGACGCAACTGTTATTGCCGAAGATGT
1321 TTCTGGTATGCCGGGCCTTAGCCGGCCTGTTTCTGAGGGAGGAATTGGTTTTGATTACCG
1381 CCTGGCAATGGCAATCCCAGATAAGTGGATAGATTATTTAAAGAATAAGAATGATGAAGA
1441 TTGGTCCATGAAGGAAGTAACATCGAGTTTGACAAATAGGAGATATACAGAGAAGTGTAT
1501 AGCATATGCGGAGAGCCATGATCAGTCTATTGTCGGTGACAAGACCATTGCATTTCTCCT
1561 AATGAACAAAGAGATGTATTCTGGCATGTCTTGCTTGACAGATGCTTCTCCTGTTGTTGA
1621 TGCAGGAATTGCGCTTGACAAGATGATCCATTTTTTTCACAATGGCCTTGGGAGGAGAGG
1681 GGTACCTCAATTTCATGGGTAACGAGTTTGGCCATCCTGAGTGGATTGACTTCCCTAGTG
1741 AGGGCAATAATTGGAGTTATGACAAATGTAGACGCCAGTGGAACCTCGCAGATAGCGAAC
1801 ACTTGAGATACAAGTTTATGAATGCATTTGATAGAGCTATGAATTCGCTCGATGAAAAGT
1861 TCTCATTCCTCGCATCAGGAAAACAGATAGTAAGCAGCATGGATGATGATAATAAGGTTG
1921 TTGTGTTTGAACGTGGTGACCTGGTATTTGTATTCAACTTCCACCCAAATAACACATACG
1981 AAGGGTATAAAGTTGGATGTGACTTGCCAGGGAAGTACAGAGTTGCACTGGACAGTGATG
2041 CTTGGGAATTTGGTGGCCATGGAAGAGCTGGTCATGATGTTGACCATTTCACATCACCAG
2101 AAGGAATACCTGGAGTTCCAGAAACAAATTTCAATGGTCGTCCAAATTCCTTCAAAGTGC
2161 TGTCTCCTGCGCGAACATGTGTGGCTTATTACAGAGTTGATGAACGCATGTCATAAACTG
2221 AAGATTACCAGACAGACATTTGTAGTGAGCTACTACCAACAGCCAATATCGAGGAAAGTG
2281 ACGAGAAACTTAAAGATTCATCATCTACAAATATCAGTACATCATCTACAAAAAATGCTT
2341 ATTACAGAGTTGATGAACGCATGTCAGAAGCTGAAGATTACCAGACAGACATTTGTAGTG
2401 AGCTACTACTACCAACAGCCAATATCGAGGAGAGTGACGAGAAACTTGATGATTCATTAT
2461 CTACAAATATCAGTAACATTGGTCAGACTGTTGTAGTTTCTGTTGAGGAGAGACAAGG
2521 AACTTAAAGATTCACCATCTGTAAGCATCATTAGTGATGCTGTTCCAGCTGAATGGGCTG
2581 ATTCGGATGCAAACGTCTGGGGTGAGGACTAGTCAGATGATTGATCGATCCTTCTACGTT
2641 GGTGATCTCGGTCCGTGCATGATGTCTTCAGGGTGGTAGCATTGACTGATTGCATCATAG
2701 TTTTTTTTTTTTTTTTAAGTATTTCCTCTATGCATATTATTAGCATCCAATAAATTTAC
2761 TGGTTGTTGTACATAGAAAAAGTGCATTTGCATGTATGTGTTTCTCTGAAATTTTCCCCA
2821 GTTTTGGTGCTTTGCCTTTGGAGCCAAGTCTCTATATGTAATAAGAAAACTAAGAACAAT
2881 CACATATATAAAATGTTAGTAGATTACCA.
```

The property of the branching enzyme to modify the amylose/amylopectin ratio in starch is not limited to a coding sequence exactly as it is shown here but can also be represented by slightly different nucleotide sequences. The property of the branching enzyme is also not changed when the plasmids containing the branching enzyme are modified in the plant cell or the plant.

To be active, the DNA sequence of the branching enzyme is fused to the regulatory sequences of other genes which guarantee a transcription of the DNA (coding) sequence of the branching enzyme. The DNA sequence can also be fused in an inverted direction to the regulatory sequences of other genes, whereby the 3'-end of the coding sequence is fused to the 3'-end of the promoter and the 5'-end of the coding sequence is fused to the 5'-end of the termination signal. In this way an anti-sense RNA of the branching enzyme is produced in the plant. The regulatory sequences herein are promoters and termination signals of plant or viral genes, such as for example the promoter of the 35S RNA of the cauliflower mosaic virus or the promoter of the class I patatin-gene B 33 and the termination signal of the 3'-end of the octopine synthase gene of the T-DNA of the Ti-plasmid pTiACH5.

Plant cells containing sequences from these plasmids can be regenerated in known manner to create transgenic plants. It is possible to insert simultaneously more than one copy of these sequences into a plant cell or plant.

The following plasmids were deposited at the Deutsche Sammlung von Mikroorganismen (DSM) in Braunschweig, Germany on the Aug. 20, 1990 (deposit number):

| Plasmid | P35 S-BE | (DSM 6143) |
| Plasmid | P35 S-anti-BE | (DSM 6144) |
| Plasmid | P33-BE | (DSM 6145) |
| Plasmid | P33-anti-BE | (DSM 6146) |

A=Fragment A (529 bp) contains the 35S promoter of the cauliflower mosaic virus (CaMV). The fragment contains the nucleotides 6909–7437 of the cauliflower mosaic virus.

B=Fragment B (2909 bp) contains the DNA fragment which codes for the branching enzyme.

C=Fragment C (192 bp) contains the polyadenylation signal of the gene 3 of the T-DNA of the Ti-plasmid pTiACH5 from the nucleotide 11749 to 11939.

Also shown are the cleavage sites described in Example 1.

Figure 2:
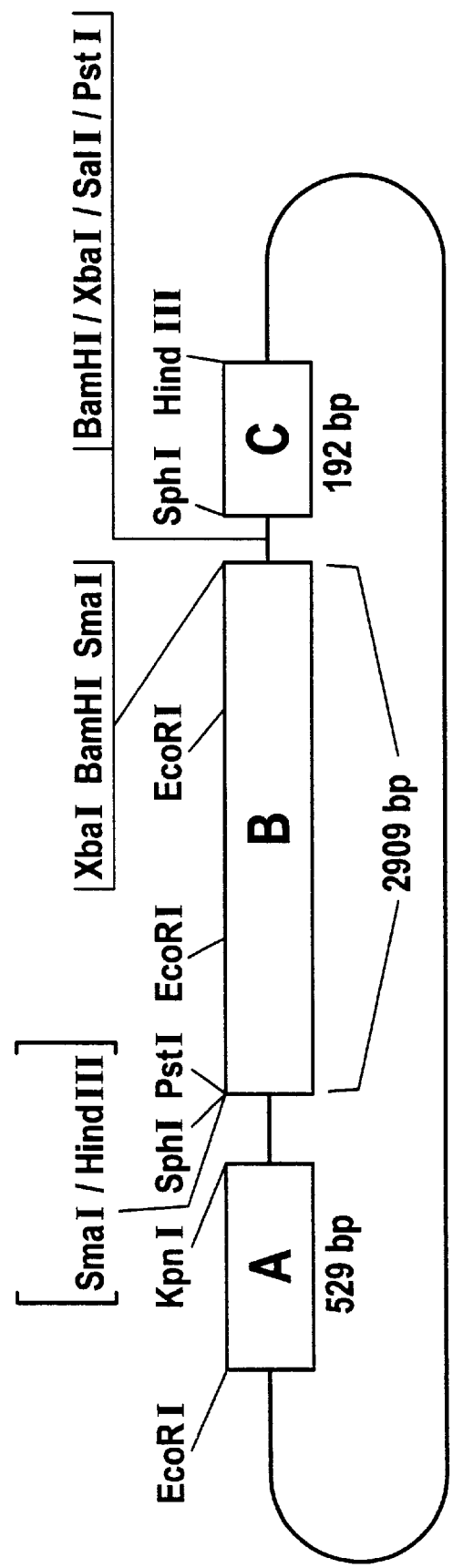

FIG. 2 shows the restriction map of the 13.6 kb plasmid P35 S-anti-BE. The plasmid contains the following fragments:

A=Fragment A (529 bp) contains the 35S promoter of the cauliflower mosaic virus (CaMV). The fragment contains the nucleotides 6909 to 7437 of the CaMV.

B=Fragment B (2909 bp) contains the DNA fragment which codes for the branching enzyme.

C=Fragment C (192 bp) contains the polyadenylation signal of gene 3 of the T-DNA of the Ti-plasmid pTiACH5. The fragment contains the nucleotides 11749–11939.

Also shown are the cleavage sites described in Example 2.

Figure 3:
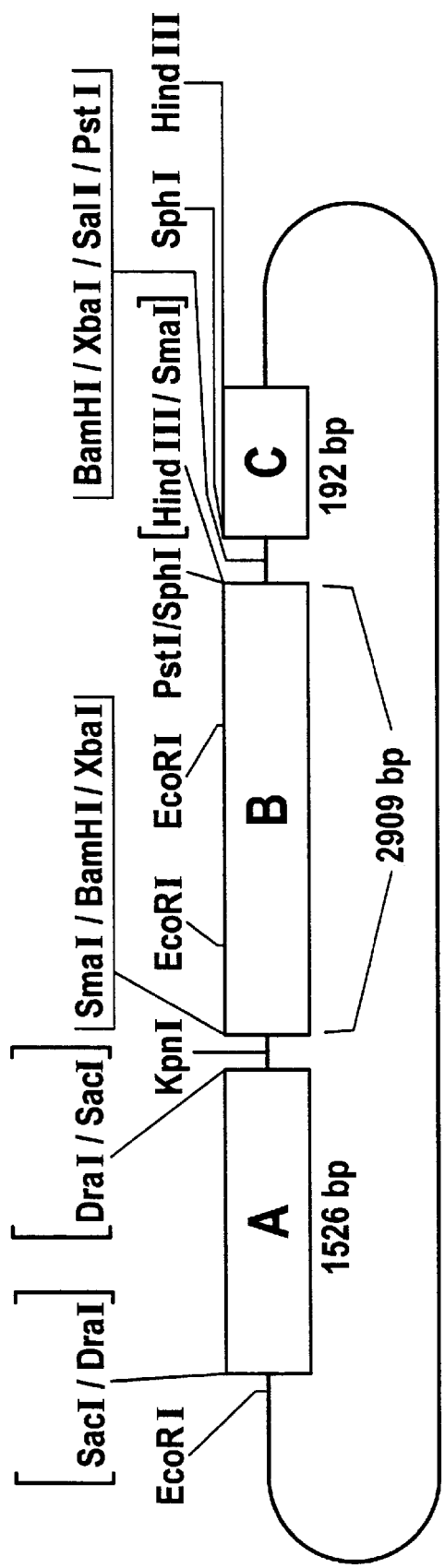

FIG. 3 shows the restriction map of the 14.6 kb plasmid P33-BE. The plasmid contains the following fragments.

A=Fragment A (1526 bp) contains the DraI—DraI-fragment of the promoter region of the patatin-gene B33. The fragment contains the nucleotide positions −1512 to +14.

B=Fragment B (2909 bp) contains the DNA fragment which codes for the branching enzyme.

C=Fragment C (192 bp) contains the polyadenylation signal of the gene 3 of the T-DNA of the Ti-plasmid pTiACH5. The fragment contains the nucleotide positions 11749–11939.

Also shown are the cleavage sites described in Example 3.

Figure 4:
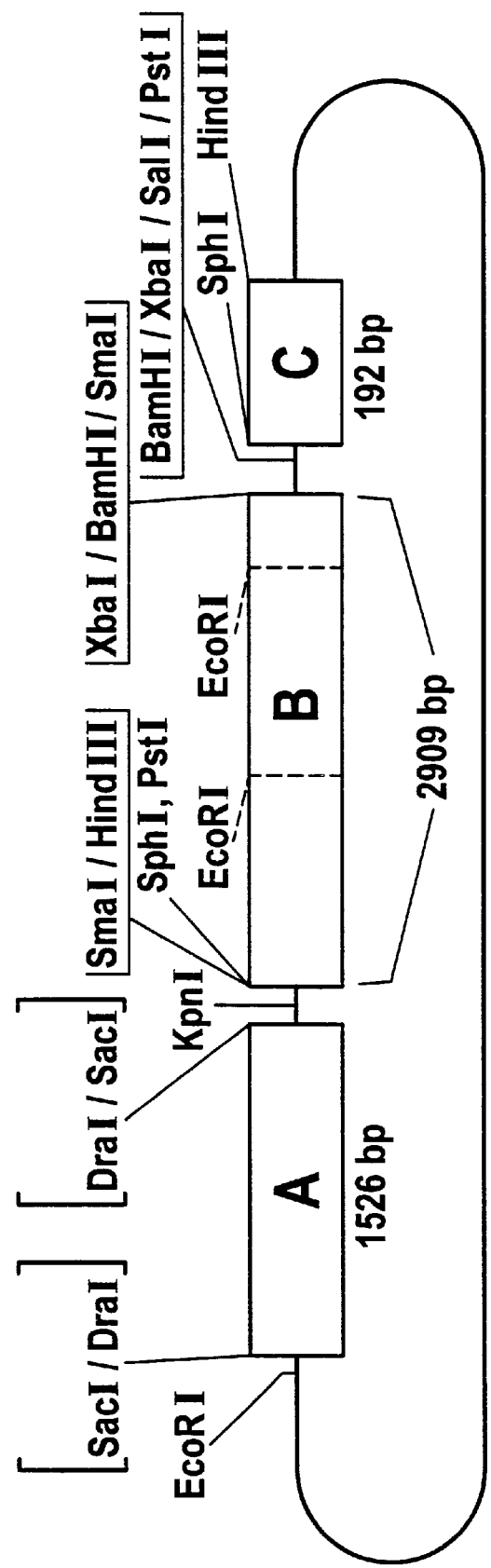

FIG. 4 shows the restriction map of the 14.6 plasmid P33-anti-BE. Plasmid contains the following fragments:

A=Fragment A (1526 bp) contains the DraI—DraI fragment of the promoter region of the patatin gene B 33. The fragment contains the nucleotide position −1512 to +14.

B=Fragment B (2909 bp) contains the cDNA-fragment which codes for the branching enzyme.

C=Fragment C (192 bp) contains the polyadenylation signal of the gene 3 of the T-DNA of the Ti-plasmid pTiACH5. The fragment contains the nucleotides 11749–11939.

Also shown are the cleavage sites described in Example 4.

Figure 5:
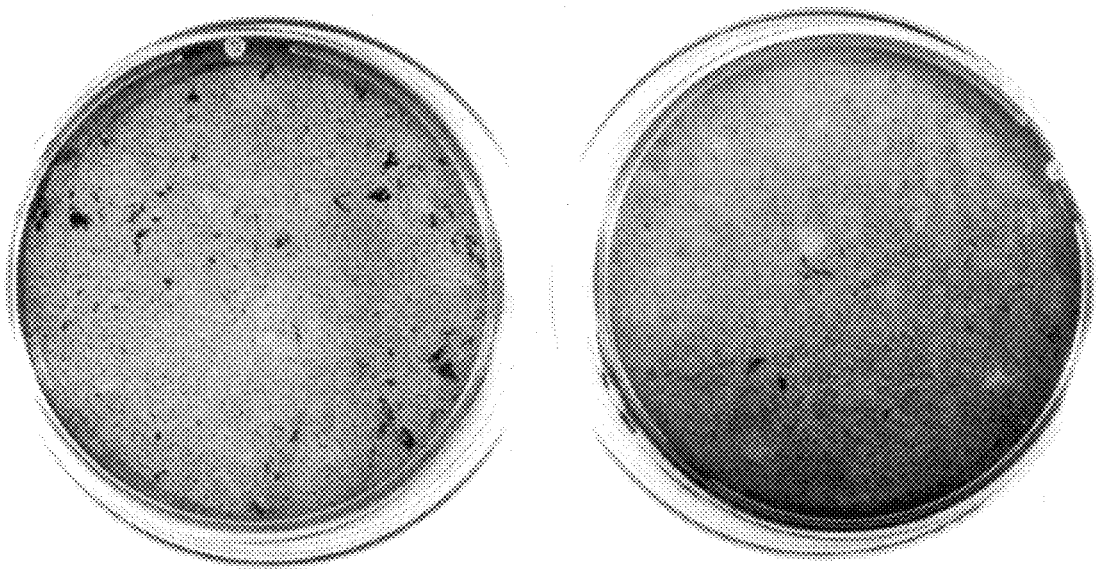

FIG. 5 shows two Petri dishes

On the right hand: Wildtype phytoglycogen (violet)

On the left hand: Modified phytoglycogen (blue).

In order to understand the examples forming the basis of this invention all the processes necessary for these tests which are known per se will first of all be listed:

1. Cloning process

The vectors pUC18/19 and pUC118, and the M13mp10 series (Yanisch-Perron et al., Gene (1985), 33, 103–119) were used for cloning.

For plant transformation, the gene constructions were cloned into the binary vector BIN19 (Bevan, Nucl. Acids Res. (1984), 12, 8711–8720).

2. Bacterial strains

The *E. coli* strain BMH71-18 (Messing et al., Proc. Natl. Acad. Sci. USA (1977), 24, 6342–6346) or TB1 was used for the pUC and M13 mP vectors.

For the vector BIN19 exclusively the *E. coli* strain TB1 was used. TB1 is a recombinant-negative, tetracycline-resistant derivative of strain JM101 (Yanisch-Perron et al., Gene (1985), 33, 103–119). The genotype of the TB1 strain is (Bart Barrel, personal communication): F'(traD36, proAB, lacI, lacZΔM15), Δ(lac, pro), SupE, this, recA, Sr1::Tn10(TCR).

The transformation of the plasmids into the potato plants was carried out by means of the *Agrobacterium tumefaciens* strain LBA4404 (Bevan, M., Nucl. Acids Res. 12, 8711–8721, (1984); BIN19 derivative).

3. Transformation of *Agrobacterium tumefaciens*

In the case of BIN19 derivatives, the insertion of the DNA into the agrobacteria was effected by direct transformation in accordance with the method developed by Holsters et al., (Mol. Gen. Genet. (1978), 163, 181–187). The plasmid DNA of transformed agrobacteria was isolated in accordance with the method developed by Birnboim and Doly (Nucl. Acids Res. (1979), 7, 1513–1523) and was separated by gel electrophoresis after suitable restriction cleavage.

4. Plant transformation 10 small leaves (wounded with a scalpel) of a sterile potato culture were placed in 10 ml of MS medium with 2% sucrose containing from 30 to 50 μl of an *Agrobacterium tumefaciens* overnight culture grown under selection. After from 3 to 5 minutes gentle shaking, the Petri dishes were incubated in the dark at 25° C. After 2 days, the leaves were laid out on MS medium with 1.6% glucose, 2 mg/l of zeatin ribose, 0.02 mg/l of naphthylacetic acid, 0.02 mg/l of gibberellic acid, 500 mg/l of claforan, 50 mg/l of kanamycin and 0.8% Bacto agar. After incubation for one week at 25° C. and 3000 lux, the claforan concentration in the medium was reduced by half. The regeneration and cultivation of the plants were carried out according to known method (Rocha-Sosa et al EMBO Journal 8, 23–29 (1989)).

5. Analysis of genomic DNA from transgenic potato plants

The isolation of genomic plant DNA was effected in accordance with Rogers and Bendich (Plant Mol. Biol. (1985), 5, 69–76).

For the DNA analysis, after suitable restriction cleavage, 10 to 20 μg of DNA were analyzed by means of Southern blots for the integration of the DNA sequences to be investigated.

6. Analysis of the total RNA from transgenic potato plants

The isolation of plant total RNA was carried out in accordance with Logemann et al. (Analytical Biochem. (1987), 163, 16–20).

For the analysis, 50 μg portions of total RNA were investigated by means of Northern blots for the presence of the transcripts sought.

7. Protein extraction

For the extraction of total protein from plant tissue, pieces of tissue were homogenized in protein extraction buffer (25 mM sodium phosphate pH 7.0, 2 mM sodium hydrogen sulphite), with the addition of 0.1% (w/v) of insoluble polyvinylpyrrolidone (PVP).

After filtration through cellulose, cell detritus was centrifuged off for 20 minutes at 10,000 revolutions per minute and the protein concentration of the supernatant was determined in accordance with the method developed by Bradford (Anal. Biochem. (1976)/72, 248–254).

8. Detection of foreign proteins by means of immunological processes (Western blot)

The protein extracts were separated according to molecular weight by means of gel electrophoresis in SDS-PAGE (sodium dodecylsulphate polyacrylamide) gels. After SDS-PAGE the protein gels were equilibrated for from 15 to 30 minutes in transfer buffer for graphite electrodes (48 g/l of tris, 39 g/l of glycine, 0.0375% SDS, 20% methanol) and then transferred in a cooling chamber to a nitrocellulose filter and separated at 1.3 mA/cm$^2$ for from 1 to 2 hours. The filter was saturated for 30 minutes with 3% gelatin in TBS buffer (20 mM tris/HCl pH 7.5, 500 mM NaCl), and the filter was then incubated for 2 hours with the appropriate antiserum in a suitable dilution (1:1000–10000 in TBS buffer) at room temperature. The filter was then washed for 15 minutes each with TBS, TTBS (TBS buffer with 0.1% polyoxyethylene-(20)-sorbitan monolaurate) and TBS buffer. After being washed, the filter was incubated for 1 hour at room temperature with alkaline phosphatase-conjugated goat-anti-rabbit (GAR) antibodies (1:7500 in TBS). The filter was then washed as described above and equilibrated in AP buffer (100 mM tris/HCl pH 9.5, 100 mM NaCl, 5 mM $MgCl_2$). The alkaline phosphatase reaction was started by means of the substrate addition of 70 μl of 4-nitrotetrazolium (NBT) solution (50 mg/ml of NBT in 70% dimethyl-formamide) and 35 μl of 5-bromo-4-chloro-3-indolyl phosphate (BCIP) (50 mg/ml BCIP in dimethylformamide) in 50 ml of AP buffer. As a rule the first signals were observed after 5 minutes.

9. Determination of the amylose/amylocectin ratio in starch of transgenic potato plants.

Leaf pieces having a diameter of 10 mm were floated in 6% sucrose solution under continuous light for 14 hours. This light incubation induced a strong increased starch formation in the leaf pieces. After incubation, the amylose and amylopectin concentration was determined according to Hovenkamp-Hermelink et al (Potato Research 31, 241–246 (1988)).

The following examples illustrate the preparation of the plasmids according to the invention; the insertion of sequences from those plasmids into the plant cell as well as regeneration of transgenic plants, and the analysis of those transgenic plants.

EXAMPLE 1

Preparation of the plasmid P35s-Be and insertion of the plasmid into the plant genome of the potato.

From a cDNA library in the expression vector λgt11, different clones were identified that cross-react with an antibody that is directed against the branching enzyme of potatoes. These clones were used to identify complete clones from a cDNA library in the HindIII-position the vector pUC 19 that originate from isolated mRNA of growing potato tubers. One clone isolated in this manner had an insert size of 2909 bp of the sequence: identified as SEQ ID NO:1

```
             10        20        30        40        50        60
  1 TCAGGAGCGGTCTTGGGATATTTCTTCCACCCCAAAATCAAGAGTTAGAAAAGATGAAAG
 61 GATGAAGCACAGTTCAGCTATTTCCGCTGTTTTGACCGATGACAATTCGACAATGGCACC
121 CCTAGAGGAAGATGTCAACACTGAAAATATTGGCCTCCTAAATTTGGATCCAACTTTGGA
181 ACCTTATCTAGATCACTTCAGACACAGAATGAAGAGATATGTGGATCAGAAAATGCTCAT
241 TGAAAAATATGAGGGACCCCTTGAGGAATTTGCTCAAGGTTATTTAAAATTTGGATTCAA
301 CAGGGAAGATGGTTGCATAGTCTATCGTGAATGGGCTCCTGCTGCTCAGGAAGCAGAAGT
```

-continued

```
 361 TATTGGCGATTTCAATGGTAGGAACGGTTCTAACCACATGATGGAGAAGGACCAGTTTGG
 421 TGTTTGGAGTATTAGAATTCCTGATGTTGACAGTAAGCCAGTCATTCCACACAACTCCAG
 481 AGTTAAGTTTCGTTTCAAACATGGTAATGGAGTGTGGGTAGATCGTATCCCTGCTTGGAT
 541 AAAGTATGCCACTGCAGACGCCACAAAGTTTGCAGCACCATATGATGGTGTCTACTGGGA
 601 CCCACCACCTTCAGAAAGGTACCACTTCAAATACCCTCGCCCTCCCAAACCCCGAGCCCC
 661 ACGAATCTACGAAGCACATGTCGGCATGAGCAGCTCTGAGCCACGTGTAAATTCGTATCG
 721 TGAGTTTGCAGATGATGTTTTACCTCGGATTAAGGCAAATAACTATAATACTGTCCAGTT
 781 GATGGCCATAATGGAACATTCTTACTATGGATCATTTGGATATCATGTTACAAACTTTTT
 841 TGCTGTGAGCAATAGATATGGAAACCCGGAGGACCTAAAGTATCTGATAGATAAAGCACA
 901 TAGCTTGGGTTTACAGGTTCTGGTGGATGTAGTTCACAGTCATGCAAGCAATAATGTCAC
 961 TGATGGCCTCAATGGCTTTGATATTGGCCAAGGTTCTCAAGAATCCTACTTTCATGCTGG
1021 AGAGCGAGGGTACCATAAGTTGTGGGATAGCAGGCTGTTCAACTATGCCAATTGGGAGGT
1081 TCTTCGTTTCCTTCTTTCCAACTTGAGGTGGTGGCTAGAAGAGTATAACTTTGACGGATT
1141 TCGATTTGATGGAATAACTTCTATGCTGTATGTTCATCATGGAATCAATATGGGATTTAC
1201 AGGAAACTATAATGAGTATTTCAGCGAGGCTACAGATGTTGATGCTGTGGTCTATTTAAT
1261 GTTGGCCAATAATCTGATTCACAAGATTTTCCCAGACGCAACTGTTATTGCCGAAGATGT
1321 TTCTGGTATGCCGGGCCTTAGCCGGCCTGTTTCTGAGGGAGGAATTGGTTTTGATTACCG
1381 CCTGGCAATGGCAATCCCAGATAAGTGGATAGATTATTTAAAGAATAAGAATGATGAAGA
1441 TTGGTCCATGAAGGAAGTAACATCGAGTTTGACAAATAGGAGATATACAGAGAAGTGTAT
1501 AGCATATGCGGAGAGCCATGATCAGTCTATTGTCGGTGACAAGACCATTGCATTTCTCCT
1561 AATGAACAAAGAGATGTATTCTGGCATGTCTTGCTTGACAGATGCTTCTCCTGTTGTTGA
1621 TGCAGGAATTGCGCTTGACAAGATGATCCATTTTTTTCACAATGGCCTTGGGAGGAGAGG
1681 GGTACCTCAATTTCATGGGTAACGAGTTTGGCCATCCTGAGTGGATTGACTTCCCTAGTG
1741 AGGGCAATAATTGGAGTTATGACAAATGTAGACGCCAGTGGAACCTCGCAGATAGCGAAC
1801 ACTTGAGATACAAGTTTATGAATGCATTTGATAGAGCTATGAATTCGCTCGATGAAAAGT
1861 TCTCATTCCTCGCATCAGGAAAACAGATAGTAAGCAGCATGGATGATGATAATAAGGTTG
1921 TTGTGTTTGAACGTGGTGACCTGGTATTTGTATTCAACTTCCACCCAAATAACACATACG
1981 AAGGGTATAAAGTTGGATGTGACTTGCCAGGGAAGTACAGAGTTGCACTGGACAGTGATG
2041 CTTGGGAATTTGGTGGCCATGGAAGAGCTGGTCATGATGTTGACCATTTCACATCACCAG
2101 AAGGAATACCTGGAGTTCCAGAAACAAATTTCAATGGTCGTCCAAATTCCTTCAAAGTGC
2161 TGTCTCCTGCGCGAACATGTGTGGCTTATTACAGAGTTGATGAACGCATGTCATAAACTG
2221 AAGATTACCAGACAGACATTTGTAGTGAGCTACTACCAACAGCCAATATCGAGGAAAGTG
2281 ACGAGAAACTTAAAGATTCATCATCTACAAATATCAGTACATCATCTACAAAAAATGCTT
2341 ATTACAGAGTTGATGAACGCATGTCAGAAGCTGAAGATTACCAGACAGACATTTGTAGTG
2401 AGCTACTACTACCAACAGCCAATATCGAGGAGAGTGACGAGAAACTTGATGATTCATTAT
2461 CTACAAATATCAGTAACATTGGTCAGACTGTTGTAGTTTCTGTTGAGGAGAGAGACAAGG
2521 AACTTAAAGATTCACCATCTGTAAGCATCATTAGTGATGCTGTTCCAGCTGAATGGGCTG
2581 ATTCGGATGCAAACGTCTGGGGTGAGGACTAGTCAGATGATTGATCGATCCTTCTACGTT
2641 GGTGATCTCGGTCCGTGCATGATGTCTTCAGGGTGGTAGCATTGACTGATTGCATCATAG
```

```
2701 TTTTTTTTTTTTTTTTTAAGTATTTCCTCTATGCATATTATTAGCATCCAATAAATTTAC

2761 TGGTTGTTGTACATAGAAAAAGTGCATTTGCATGTATGTGTTTCTCTGAAATTTTCCCCA

2821 GTTTTGGTGCTTTGCCTTTGGAGCCAAGTCTCTATATGTAATAAGAAAACTAAGAACAAT

2881 CACATATATAAAATGTTAGTAGATTACCA.
```

The 2909 bp long c-DNA contained in this clone was used for the next examples and is called cBE.

For the preparation of a plasmid p35s-BE, this cDNA was provided with the promoter of the 35s-RNA of the cauliflower mosaic virus as well as the polyadenylation signal of the octopine synthase gene of the Ti-plasmid pTiACH5. For this the orientation of the C-DNA coding for the branching enzyme was chosen in such a way that the coding strain will be readable (sense-orientation). The plasmid p35s-BE has a size of 13.6 kb and comprises the three fragments A, B and C which were cloned into the cleavage sites of the polylinker of BIN19.

Fragment A (529 bp) contains the 35s promoter of the cauliflower mosaic virus (CaMV). The fragment contains the nucleotides 6909 to 7437 of the CaMV (Franck et al., Cell 21, 285–294). It was isolated as EcoRI-KpnI-fragment from the plasmid pDH51 (Pietrzak et al, Nucleic Acids Research 14, 5857–5868) and was cloned between the EcoRI-KpnI-cleavage position of the polylinker of the plasmid BIN 19.

Fragment B contains a 2909 bp cDNA fragment cBe which codes for the branching enzyme. It was cut out as HindIII-SmaI-fragment of the vector pUC 19 and was cloned into the SmaI-position of the polylinker of BIN 19 after filling-in of the Hind-III-position with DNA polymerase. For this the orientation of the cDNA was chosen in such a way that the coding strand is readable and a sense-RNA is formed. The cleavage sites BamHI/XbaI and PstI/SphI originate from the polylinker of pUC 19. The cleavage sites BamHI/XbaI/SalI/PstI originate from the polylinker of BIN 19. The two EcoRI cleavage sites located on the fragment B are internal cleavage sites of the fragment.

Figure 1:
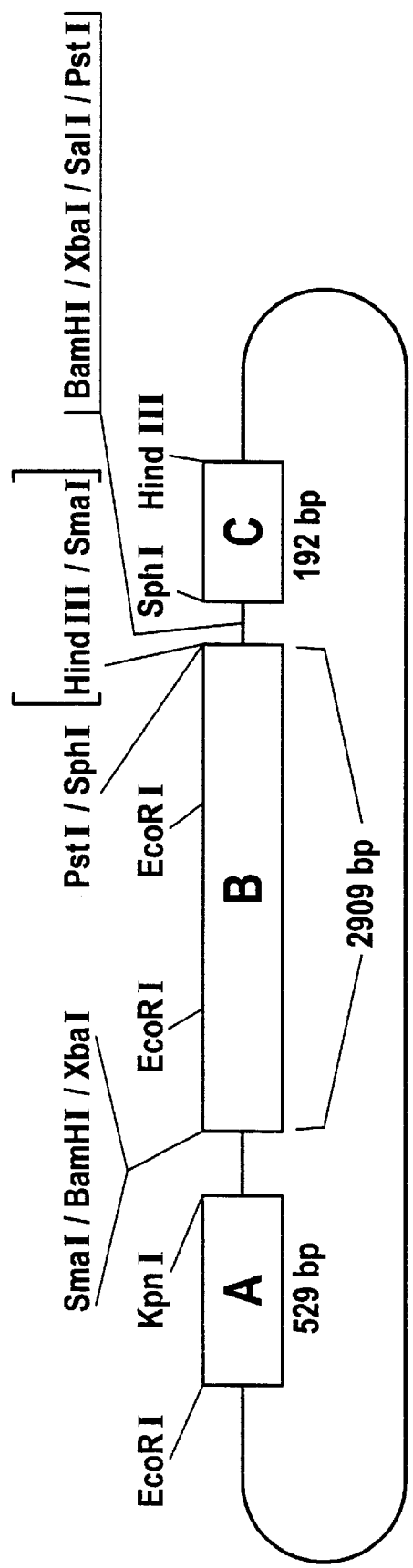
FIG. 1 shows the restriction map of the 13.6 kb plasmid P35 S-BE. The plasmid contains the following fragments.

Fragment C (192 bp) contains the polyadenylation signal of the gene 3 of the T-DNA of the Ti-plasmid pTiACH5 (Gielen et al EMBO J. 3, 835,846), nucleotides 11749–11939, which are isolated as PvuII-HindIII fragment from the plasmid pAGV 40 (Herrera-Estrella et al (1983) Nature 303, 209–213) and were then cloned onto the PvuII cleavage site between the SphI-Hind-III cleavage site of the polylinker of BIN 19, after addition of SphI linkers (see FIG. 1).

The plasmid p35s-BE was transferred into potatoes with the help of the agrobacterial system. After this whole plants were regenerated. Protein extracts isolated from tubers of these plants were tested for the existence of the branching enzyme using the western blot analysis. Further, tubers of these plants were tested for the content of amylose and amylopectin.

EXAMPLE 2

Preparation of the plasmid p35s-anti-BE and introduction of the plasmid the plant genome of potato.

In a similar manner to that described in Example 1, the plasmid p35s-anti-BE was prepared, but the orientation of the designated cDNA of the branching enzyme was inverted relative to the 35 S promotor. The plasmid p35s-anti-BE has a size of 13.6 kb and comprises the three fragments A, B and C which were cloned in the cleavage sites of the polylinker of BIN19.

Fragment A (529 bp) contains the 35s promoter of the cauliflower mosaic virus (CaMV). The fragment contains the nucleotides 6909 to 7437 of the CaMV (Franck et al. Cell 21, 285–294), and was isolated as EcoRI-KpnI-fragment from the plasmid pDH51 (Pietrzak et al Nucleic Acids Research 14, 5857–5868) and cloned between the EcoRI-KpnI-cleavage site of the polylinker of the plasmid BIN 19.

Fragment B contains the 2909 bp cDNA fragment cBE which codes for the branching enzyme. It was cut from the HindIII-SmaI-fragment of the vector pUC 19 and cloned in the SmaI-position of the polylinker BIN 19 after filling in of the HindIII-position with DNA polymerase. The orientation was chosen in such a way that the non-coding strand is readable and an anti-sense-RNA is formed. The cleavage sites SphI, PstI and XbaI, BamHI, SmaI originate from the polylinker pUC 19. The cutting positions BamHI/XbaI/SalI/PstI originate from the polylinker of BIN 19. The two EcoRI cleavage sides contained on the fragment B are internal cleavage sides of this fragment.

Fragment C (192 bp) contains the polyadenylation signal of gene 3 of the T-DNA of the TI-plasmid pTiACH5 (Gielen et al EMBO J 3, 835–846), nucleotides 11749–11939, which were isolated as PvuII-HindIII-fragment from the plasmid pAGV 40 (Herrera-Estrella et al (1983), and which were cloned between the SphI-HindIII-cleavage position of the polylinker of BIN 19 after addition of Sph-I-linkers to the Pvu-II-cleavage position (see FIG. 2).

The plasmid p35s-anti-BE was transferred into potatoes using the agrobacterial system. After this whole plants were regenerated.

Protein extracts, which had been isolated from tubers of these plants, were tested for the existence of the branching enzyme using the western blot analysis. Tubers of these plants were also tested for the content of amylose and amylopectin.

EXAMPLE 3

Preparation of the plasmid p33-BE and introduction of the plasmid into the plant genome of the potato.

In a similar manner to that described in Example 1, the plasmid p33-BE was prepared, but replacing the 35s promoter with the promoter of the class I patatin-gene B33 (Rocha-Sosa et al EMBO J 8 23–29). The plasmid p33-Be has a size of 14.6 kb and consists of the three fragments A, B and C that were cloned into the cleavage position of the polylinker of BIN 19.

Fragment A contains the DraI—DraI-fragment (position −1512 to position +14) of the promoter region of the patatin-gene B33 (Rocha-Sosa et al EMBO J 8. 23–29), which was first of all cloned into the SacI-position of the polylinker of pUC 18. For this the overhanging 3'-end of the Sac-I-cleavage site had been rendered blunt by T4-DNA polymerase. After this the EcoRI-BamHI-fragment was inserted between the EcoRI-BamHI-position of the polylinker of BIN 19.

Fragment B contains the 2909 bp cDNA fragment cBE which codes for the branching enzyme. It was cut out as HindIII-SmaI-fragment from the vector pUC 19 and was cloned into the SmaI-position of the polylinker of BIN 19 after the HindIII-position was filled in with DNA polymerase. For this the orientation of the cDNA was chosen in such a way that the coding strand was readable and a sense-RNA was formed. The cleavage sites BamHI/XbaI and PstI/SphI originate from the polylinker of pUC 19. The cutting positions BamHI/XbaI/SalI/PstI originate from the polylinker of BIN 19. The two EcoRI-cleavage sites contained on the fragment B are internal cleavage sites of this fragment.

Fragment C (192 bp) contains the polyadenylation signal of gene 3 of the T-DNA of the Ti-plasmid PtiACH5 (Gielen et al EMBO J 3, 835–846, Nucleotide 11749–11939), which was isolated as Pvu-II-HindIII-fragment from the plasmid pAGV 40 (Herrera-Estrella et al (1983) Nature 303, 209–213) and which was cloned between the sphI-HindIII-cleavage site of the polylinker of BIN 19 after addition of SphI-linkers to the PvuII-cleavage site.

The plasmid p33-BE was transferred into *Agrobacterium tumefaciens* and used for the transformation of potato plants.

EXAMPLE 4

Preparation of the plasmid p33-anti-BE and introduction of plasmid into the plant genome of potato.

In a similar manner to that described in Example 2, plasmid p33-anti-BE was prepared but replacing the 35S-promoter with the promoter of the class I patatin-gene B33 (Rocha-Sosa et al EMBO J 8, 23–29). The plasmid p33-anti-Be has a size of 14.6 kb and consists of three fragments A, B and C which were cloned into the cleavage sites of the polylinker of BIN 19.

Fragment A contains the DraI—DraI-fragment (position −1512 to position +14) of the promoter region of the patatin-gene B33 (Rocha-Sosa et al EMBO J 8, 23–29) which was firstly cloned into the SacI-position of the polylinker of pUC 18. The overhanging 3'-ends of the SacI-cleavage site were rendered blunt by T4-DNA polymerase. After this the fragment was inserted as EcoRI-BamHI-fragment between the EcoRI-BamHI-position of the polylinker of BIN 19.

Fragment B contains the 2909 bp cDNA fragment cBE which codes for the branching enzyme. It was cut out as HindIII-SmaI-fragment from the vector pUC 18 and after filling in the HindIII-position with the DNA polymerase, it was cloned into the SmaI-position of the polylinker of BIN 19. For this the orientation of the cDNA was chosen in such a manner that the non-coding strand was readable and anti-sense-RNA could be formed. The cutting positions SphI, PstI and XbaI, BamHI, SmaI originate from the polylinker of pUC 19. The cutting positions BamHI/XbaI/SalI/PstI originate from the polylinker of BIN 19. The two EcoRI cleavage sites which are located on the fragment B are internal cleavage sites of the fragment.

Fragment C (192 bp) contains the polyadenylation signal of the gene 3 of the T-DNA of the Ti-plasmid pTiACH5 (Gielen et al EMBO J 3, 835–846), Nucleotides 11749–11939), which had been isolated as PvuII-HindIII-fragment from the plasmid pAGV 40 (Herrera-Estrella et al (1983), Nature 303, 209–213) and which was cloned between the SphI-HindIII-cleavage site of the polylinker of BIN 19 after addition of SphI-linkers to the PvuII cleavage sites.

The plasmid p33-anti-BE was introduced in *Agrobacterium tumefaciens* and was used for the transformation of potato plants.

EXAMPLE 5

The nucleotides 166–2909 of the 2909 bp cDNA sequence described in Example 1 which code for the branching enzyme in the HindII-cleavage site of the cloning vector pUC 19, were inserted into the corresponding cleavage sites of the polylinker of the cloning vector pUC 18. This makes possible a fusion of the N-end of the α-peptide of the β-galactosidase located on the vector with a part of the branching enzyme. The functionality of the resulting fusion protein was tested in a mutant of *Escherichia coli* (KV 832) which is deficient in the branching enzyme (Kiel et al Gene 78, 9–17). Cells transformed with this construction were plated out on YT-agar plates containing 0.5% glucose. The resulting colonies were stained with Lugolscher solution. The transformed plant cells showed a yellow-red color in contrast to the blue colored untransformed plant cells which indicates the branching activity of the fusion protein (Kiel et al Gene 78, 9–17). An overproduction of this protein in *Escherichia coli* enables its use as technical enzyme.

EXAMPLE

Iodine staining of soluble components of tuber material

Starch in principal is present in the plant cell as a water insoluble compound, but can be solubilised in part, for example by heating. The following procedure describes a qualitative discrimination of unbranched and branched phytoglycogen that are water soluble under the experimental procedure.

Potato tuber material is grinded in a mortar and suspended in 50 mM Tris/HCl (pH 7.5). The suspension is mixed with an equal volume of 2% Agarose in hot water. The mixture is poured into Petri dishes and after hardening stained with LUGOL's solution for 30 minutes. The result of a typical analysis of transgenic plants transformed by plasmids p35S-anti-BE or p33-anti-BE respectively is shown in FIG. 5.

As shown in the figure, the wildtype phytoglycogen are staining violet because of the presence of blue staining amylose and red staining branched polyglucans. In the tuber extracts of modified plants solely the blue staining of amylose can be seen.

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:

```
       (A) LENGTH: 2909 base pairs
       (B) TYPE: nucleic acid
       (C) STRANDEDNESS: double
       (D) TOPOLOGY: linear (ii) MOLECULE TYPE: cDNA to mRNA (iii) HYPOTHETICAL: NO (iv) ANTI-SENSE: NO (vi) ORIGINAL SOURCE:
       (A) ORGANISM: Solanum tuberosum cv. Desiree
       (B) STRAIN: Desiree
       (D) DEVELOPMENTAL STAGE: growing tuber
       (F) TISSUE TYPE: tuber
       (G) CELL TYPE: total tuber (vii) IMMEDIATE SOURCE:
       (A) LIBRARY: cDNA of total tuber mRNA in pUC 19 (Hinc II)

(ix) FEATURE:
       (A) NAME/KEY: CDS
       (B) LOCATION: 2..1699
       (D) OTHER INFORMATION: /note= "for Branching enzyme I
           (partial) truncated protein; 97,11 % identity to
           active potato branching enzyme"

(xi) SEQUENCE DESCRIPTION: SEQ ID NO:1:
```

```
T CAG GAG CGG TCT TGG GAT ATT TCT TCC ACC CCA AAA TCA AGA GTT         46
  Gln Glu Arg Ser Trp Asp Ile Ser Ser Thr Pro Lys Ser Arg Val
  1               5                  10                  15

AGA AAA GAT GAA AGG ATG AAG CAC AGT TCA GCT ATT TCC GCT GTT TTG       94
Arg Lys Asp Glu Arg Met Lys His Ser Ser Ala Ile Ser Ala Val Leu
                20                  25                  30

ACC GAT GAC AAT TCG ACA ATG GCA CCC CTA GAG GAA GAT GTC AAC ACT      142
Thr Asp Asp Asn Ser Thr Met Ala Pro Leu Glu Glu Asp Val Asn Thr
            35                  40                  45

GAA AAT ATT GGC CTC CTA AAT TTG GAT CCA ACT TTG GAA CCT TAT CTA      190
Glu Asn Ile Gly Leu Leu Asn Leu Asp Pro Thr Leu Glu Pro Tyr Leu
        50                  55                  60

GAT CAC TTC AGA CAC AGA ATG AAG AGA TAT GTG GAT CAG AAA ATG CTC      238
Asp His Phe Arg His Arg Met Lys Arg Tyr Val Asp Gln Lys Met Leu
    65                  70                  75

ATT GAA AAA TAT GAG GGA CCC CTT GAG GAA TTT GCT CAA GGT TAT TTA      286
Ile Glu Lys Tyr Glu Gly Pro Leu Glu Glu Phe Ala Gln Gly Tyr Leu
80                  85                  90                  95

AAA TTT GGA TTC AAC AGG GAA GAT GGT TGC ATA GTC TAT CGT GAA TGG      334
Lys Phe Gly Phe Asn Arg Glu Asp Gly Cys Ile Val Tyr Arg Glu Trp
                100                 105                 110

GCT CCT GCT GCT CAG GAA GCA GAA GTT ATT GGC GAT TTC AAT GGT AGG      382
Ala Pro Ala Ala Gln Glu Ala Glu Val Ile Gly Asp Phe Asn Gly Arg
            115                 120                 125

AAC GGT TCT AAC CAC ATG ATG GAG AAG GAC CAG TTT GGT GTT TGG AGT      430
Asn Gly Ser Asn His Met Met Glu Lys Asp Gln Phe Gly Val Trp Ser
        130                 135                 140

ATT AGA ATT CCT GAT GTT GAC AGT AAG CCA GTC ATT CCA CAC AAC TCC      478
Ile Arg Ile Pro Asp Val Asp Ser Lys Pro Val Ile Pro His Asn Ser
    145                 150                 155

AGA GTT AAG TTT CGT TTC AAA CAT GGT AAT GGA GTG TGG GTA GAT CGT      526
Arg Val Lys Phe Arg Phe Lys His Gly Asn Gly Val Trp Val Asp Arg
160                 165                 170                 175

ATC CCT GCT TGG ATA AAG TAT GCC ACT GCA GAC GCC ACA AAG TTT GCA      574
Ile Pro Ala Trp Ile Lys Tyr Ala Thr Ala Asp Ala Thr Lys Phe Ala
                180                 185                 190

GCA CCA TAT GAT GGT GTC TAC TGG GAC CCA CCA CCT TCA GAA AGG TAC      622
```

-continued

```
Ala Pro Tyr Asp Gly Val Tyr Trp Asp Pro Pro Ser Glu Arg Tyr
            195                 200                 205

CAC TTC AAA TAC CCT CGC CCT CCC AAA CCC CGA GCC CCA CGA ATC TAC        670
His Phe Lys Tyr Pro Arg Pro Pro Lys Pro Arg Ala Pro Arg Ile Tyr
            210                 215                 220

GAA GCA CAT GTC GGC ATG AGC AGC TCT GAG CCA CGT GTA AAT TCG TAT        718
Glu Ala His Val Gly Met Ser Ser Ser Glu Pro Arg Val Asn Ser Tyr
            225                 230                 235

CGT GAG TTT GCA GAT GAT GTT TTA CCT CGG ATT AAG GCA AAT AAC TAT        766
Arg Glu Phe Ala Asp Asp Val Leu Pro Arg Ile Lys Ala Asn Asn Tyr
240                 245                 250                 255

AAT ACT GTC CAG TTG ATG GCC ATA ATG GAA CAT TCT TAC TAT GGA TCA        814
Asn Thr Val Gln Leu Met Ala Ile Met Glu His Ser Tyr Tyr Gly Ser
                260                 265                 270

TTT GGA TAT CAT GTT ACA AAC TTT TTT GCT GTG AGC AAT AGA TAT GGA        862
Phe Gly Tyr His Val Thr Asn Phe Phe Ala Val Ser Asn Arg Tyr Gly
                275                 280                 285

AAC CCG GAG GAC CTA AAG TAT CTG ATA GAT AAA GCA CAT AGC TTG GGT        910
Asn Pro Glu Asp Leu Lys Tyr Leu Ile Asp Lys Ala His Ser Leu Gly
                290                 295                 300

TTA CAG GTT CTG GTG GAT GTA GTT CAC AGT CAT GCA AGC AAT AAT GTC        958
Leu Gln Val Leu Val Asp Val Val His Ser His Ala Ser Asn Asn Val
305                 310                 315

ACT GAT GGC CTC AAT GGC TTT GAT ATT GGC CAA GGT TCT CAA GAA TCC       1006
Thr Asp Gly Leu Asn Gly Phe Asp Ile Gly Gln Gly Ser Gln Glu Ser
320                 325                 330                 335

TAC TTT CAT GCT GGA GAG CGA GGG TAC CAT AAG TTG TGG GAT AGC AGG       1054
Tyr Phe His Ala Gly Glu Arg Gly Tyr His Lys Leu Trp Asp Ser Arg
                340                 345                 350

CTG TTC AAC TAT GCC AAT TGG GAG GTT CTT CGT TTC CTT CTT TCC AAC       1102
Leu Phe Asn Tyr Ala Asn Trp Glu Val Leu Arg Phe Leu Leu Ser Asn
                355                 360                 365

TTG AGG TGG TGG CTA GAA GAG TAT AAC TTT GAC GGA TTT CGA TTT GAT       1150
Leu Arg Trp Trp Leu Glu Glu Tyr Asn Phe Asp Gly Phe Arg Phe Asp
                370                 375                 380

GGA ATA ACT TCT ATG CTG TAT GTT CAT CAT GGA ATC AAT ATG GGA TTT       1198
Gly Ile Thr Ser Met Leu Tyr Val His His Gly Ile Asn Met Gly Phe
            385                 390                 395

ACA GGA AAC TAT AAT GAG TAT TTC AGC GAG GCT ACA GAT GTT GAT GCT       1246
Thr Gly Asn Tyr Asn Glu Tyr Phe Ser Glu Ala Thr Asp Val Asp Ala
400                 405                 410                 415

GTG GTC TAT TTA ATG TTG GCC AAT AAT CTG ATT CAC AAG ATT TTC CCA       1294
Val Val Tyr Leu Met Leu Ala Asn Asn Leu Ile His Lys Ile Phe Pro
                420                 425                 430

GAC GCA ACT GTT ATT GCC GAA GAT GTT TCT GGT ATG CCG GGC CTT AGC       1342
Asp Ala Thr Val Ile Ala Glu Asp Val Ser Gly Met Pro Gly Leu Ser
                435                 440                 445

CGG CCT GTT TCT GAG GGA GGA ATT GGT TTT GAT TAC CGC CTG GCA ATG       1390
Arg Pro Val Ser Glu Gly Gly Ile Gly Phe Asp Tyr Arg Leu Ala Met
            450                 455                 460

GCA ATC CCA GAT AAG TGG ATA GAT TAT TTA AAG AAT AAG AAT GAT GAA       1438
Ala Ile Pro Asp Lys Trp Ile Asp Tyr Leu Lys Asn Lys Asn Asp Glu
            465                 470                 475

GAT TGG TCC ATG AAG GAA GTA ACA TCG AGT TTG ACA AAT AGG AGA TAT       1486
Asp Trp Ser Met Lys Glu Val Thr Ser Ser Leu Thr Asn Arg Arg Tyr
480                 485                 490                 495

ACA GAG AAG TGT ATA GCA TAT GCG GAG AGC CAT GAT CAG TCT ATT GTC       1534
Thr Glu Lys Cys Ile Ala Tyr Ala Glu Ser His Asp Gln Ser Ile Val
                500                 505                 510
```

```
GGT GAC AAG ACC ATT GCA TTT CTC CTA ATG AAC AAA GAG ATG TAT TCT          1582
Gly Asp Lys Thr Ile Ala Phe Leu Leu Met Asn Lys Glu Met Tyr Ser
            515                 520                 525

GGC ATG TCT TGC TTG ACA GAT GCT TCT CCT GTT GTT GAT GCA GGA ATT          1630
Gly Met Ser Cys Leu Thr Asp Ala Ser Pro Val Val Asp Ala Gly Ile
        530                 535                 540

GCG CTT GAC AAG ATG ATC CAT TTT TTT CAC AAT GGC CTT GGG AGG AGA          1678
Ala Leu Asp Lys Met Ile His Phe Phe His Asn Gly Leu Gly Arg Arg
        545                 550                 555

GGG GTA CCT CAA TTT CAT GGG TAACGAGTTT GGCCATCCTG AGTGGATTGA             1729
Gly Val Pro Gln Phe His Gly
560                 565

CTTCCCTAGT GAGGGCAATA ATTGGAGTTA TGACAAATGT AGACGCCAGT GGAACCTCGC        1789

AGATAGCGAA CACTTGAGAT ACAAGTTTAT GAATGCATTT GATAGAGCTA TGAATTCGCT        1849

CGATGAAAAG TTCTCATTCC TCGCATCAGG AAAACAGATA GTAAGCAGCA TGGATGATGA        1909

TAATAAGGTT GTTGTGTTTG AACGTGGTGA CCTGGTATTT GTATTCAACT TCCACCCAAA        1969

TAACACATAC GAAGGGTATA AAGTTGGATG TGACTTGCCA GGGAAGTACA GAGTTGCACT        2029

GGACAGTGAT GCTTGGGAAT TTGGTGGCCA TGGAAGAGCT GGTCATGATG TTGACCATTT        2089

CACATCACCA GAAGGAATAC CTGGAGTTCC AGAAACAAAT TTCAATGGTC GTCCAAATTC        2149

CTTCAAAGTG CTGTCTCCTG CGCGAACATG TGTGGCTTAT TACAGAGTTG ATGAACGCAT        2209

GTCATAAACT GAAGATTACC AGACAGACAT TTGTAGTGAG CTACTACCAA CAGCCAATAT        2269

CGAGGAAAGT GACGAGAAAC TTAAAGATTC ATCATCTACA AATATCAGTA CATCATCTAC        2329

AAAAAATGCT TATTACAGAG TTGATGAACG CATGTCAGAA GCTGAAGATT ACCAGACAGA        2389

CATTTGTAGT GAGCTACTAC TACCAACAGC CAATATCGAG GAGAGTGACG AGAAACTTGA        2449

TGATTCATTA TCTACAAATA TCAGTAACAT TGGTCAGACT GTTGTAGTTT CTGTTGAGGA        2509

GAGAGACAAG GAACTTAAAG ATTCACCATC TGTAAGCATC ATTAGTGATG CTGTTCCAGC        2569

TGAATGGGCT GATTCGGATG CAAACGTCTG GGGTGAGGAC TAGTCAGATG ATTGATCGAT        2629

CCTTCTACGT TGGTGATCTC GGTCCGTGCA TGATGTCTTC AGGGTGGTAG CATTGACTGA        2689

TTGCATCATA GTTTTTTTTT TTTTTTTAA GTATTTCCTC TATGCATATT ATTAGCATCC        2749

AATAAATTTA CTGGTTGTTG TACATAGAAA AAGTGCATTT GCATGTATGT GTTTCTCTGA        2809

AATTTTCCCC AGTTTTGGTG CTTTGCCTTT GGAGCCAAGT CTCTATATGT AATAAGAAAA        2869

CTAAGAACAA TCACATATAT AAAATGTTAG TAGATTACCA                               2909

(2) INFORMATION FOR SEQ ID NO:2:

(i) SEQUENCE CHARACTERISTICS:
        (A) LENGTH: 566 amino acids
        (B) TYPE: amino acid
        (D) TOPOLOGY: linear (ii) MOLECULE TYPE: protein (xi) SEQUENCE DESCRIPTION: SEQ ID NO:2:

Gln Glu Arg Ser Trp Asp Ile Ser Ser Thr Pro Lys Ser Arg Val Arg
  1               5                  10                  15

Lys Asp Glu Arg Met Lys His Ser Ser Ala Ile Ser Ala Val Leu Thr
              20                  25                  30

Asp Asp Asn Ser Thr Met Ala Pro Leu Glu Glu Asp Val Asn Thr Glu
          35                  40                  45

Asn Ile Gly Leu Leu Asn Leu Asp Pro Thr Leu Glu Pro Tyr Leu Asp
      50                  55                  60
```

```
His Phe Arg His Arg Met Lys Arg Tyr Val Asp Gln Lys Met Leu Ile
65                  70                  75                  80

Glu Lys Tyr Glu Gly Pro Leu Glu Glu Phe Ala Gln Gly Tyr Leu Lys
                85                  90                  95

Phe Gly Phe Asn Arg Glu Asp Gly Cys Ile Val Tyr Arg Glu Trp Ala
                100                 105                 110

Pro Ala Ala Gln Glu Ala Glu Val Ile Gly Asp Phe Asn Gly Arg Asn
            115                 120                 125

Gly Ser Asn His Met Met Glu Lys Asp Gln Phe Gly Val Trp Ser Ile
        130                 135                 140

Arg Ile Pro Asp Val Asp Ser Lys Pro Val Ile Pro His Asn Ser Arg
145                 150                 155                 160

Val Lys Phe Arg Phe Lys His Gly Asn Gly Val Trp Val Asp Arg Ile
                165                 170                 175

Pro Ala Trp Ile Lys Tyr Ala Thr Ala Asp Ala Thr Lys Phe Ala Ala
                180                 185                 190

Pro Tyr Asp Gly Val Tyr Trp Asp Pro Pro Ser Glu Arg Tyr His
            195                 200                 205

Phe Lys Tyr Pro Arg Pro Pro Lys Pro Arg Ala Pro Arg Ile Tyr Glu
            210                 215                 220

Ala His Val Gly Met Ser Ser Ser Glu Pro Arg Val Asn Ser Tyr Arg
225                 230                 235                 240

Glu Phe Ala Asp Asp Val Leu Pro Arg Ile Lys Ala Asn Asn Tyr Asn
                245                 250                 255

Thr Val Gln Leu Met Ala Ile Met Glu His Ser Tyr Tyr Gly Ser Phe
            260                 265                 270

Gly Tyr His Val Thr Asn Phe Phe Ala Val Ser Asn Arg Tyr Gly Asn
        275                 280                 285

Pro Glu Asp Leu Lys Tyr Leu Ile Asp Lys Ala His Ser Leu Gly Leu
    290                 295                 300

Gln Val Leu Val Asp Val Val His Ser His Ala Ser Asn Asn Val Thr
305                 310                 315                 320

Asp Gly Leu Asn Gly Phe Asp Ile Gly Gln Gly Ser Gln Glu Ser Tyr
                325                 330                 335

Phe His Ala Gly Glu Arg Gly Tyr His Lys Leu Trp Asp Ser Arg Leu
            340                 345                 350

Phe Asn Tyr Ala Asn Trp Glu Val Leu Arg Phe Leu Leu Ser Asn Leu
        355                 360                 365

Arg Trp Trp Leu Glu Glu Tyr Asn Phe Asp Gly Phe Arg Phe Asp Gly
370                 375                 380

Ile Thr Ser Met Leu Tyr Val His His Gly Ile Asn Met Gly Phe Thr
385                 390                 395                 400

Gly Asn Tyr Asn Glu Tyr Phe Ser Glu Ala Thr Asp Val Asp Ala Val
                405                 410                 415

Val Tyr Leu Met Leu Ala Asn Asn Leu Ile His Lys Ile Phe Pro Asp
            420                 425                 430

Ala Thr Val Ile Ala Glu Asp Val Ser Gly Met Pro Gly Leu Ser Arg
        435                 440                 445

Pro Val Ser Glu Gly Gly Ile Gly Phe Asp Tyr Arg Leu Ala Met Ala
    450                 455                 460

Ile Pro Asp Lys Trp Ile Asp Tyr Leu Lys Asn Lys Asn Asp Glu Asp
465                 470                 475                 480
```

```
Trp Ser Met Lys Glu Val Thr Ser Ser Leu Thr Asn Arg Arg Tyr Thr
            485             490                 495

Glu Lys Cys Ile Ala Tyr Ala Glu Ser His Asp Gln Ser Ile Val Gly
            500             505             510

Asp Lys Thr Ile Ala Phe Leu Leu Met Asn Lys Glu Met Tyr Ser Gly
            515             520             525

Met Ser Cys Leu Thr Asp Ala Ser Pro Val Val Asp Ala Gly Ile Ala
        530             535             540

Leu Asp Lys Met Ile His Phe Phe His Asn Gly Leu Gly Arg Arg Gly
545             550             555                 560

Val Pro Gln Phe His Gly
                565
```

What is claimed is:

1. A composition comprising nucleic acid molecules comprising an isolated DNA sequence encoding a plant branching enzyme from potato, said enzyme participating in the formation of α-1,6 linkages of glucose monomers, wherein the plant branching enzyme sequence comprises the following sequence, identified as SEQ ID NO: 1:

```
              10        20        30        40        50        60
   1 TCAGGAGCGGTCTTGGGATATTTCTTCCACCCCAAAATCAAGAGTTAGAAAAGATGAAAG
  51 GATGAAGCACAGTTCAGCTATTTCCGCTGTTTTGACCGATGACAATTCGACAATGGCACC
 121 CCTAGAGGAAGATGTCAACACTGAAAATATTGGCCTCCTAAATTTGGATCCAACTTTGGA
 181 ACCTTATCTAGATCACTTCAGACACAGAATGAAGAGATATGTGGATCAGAAAATGCTCAT
 241 TGAAAAATATGAGGGACCCCTTGAGGAATTTGCTCAAGGTTATTTAAAATTTGGATTCAA
 301 CAGGGAAGATGGTTGCATAGTCTATCGTGAATGGGCTCCTGCTGCTCAGGAAGCAGAAGT
 361 TATTGGCGATTTCAATGGTAGGAACGGTTCTAACCACATGATGGAGAAGGACCAGTTTGG
 541 AAAGTATGCCACTGCAGACGCCACAAAGTTTGCAGCACCATATGATGGTGTCTACTGGGA
 601 CCCACCACCTTCAGAAAGGTACCACTTCAAATACCCTCGCCCTCCCAAACCCCGAGCCCC
 661 ACGAATCTACGAAGCACATGTCGGCATGAGCAGCTCTGAGCCACGTGTAAATTCGTATCG
 721 TGAGTTTGCAGATGATGTTTTACCTCGGATTAAGGCAAATAACTATAATACTGTCCAGTT
 781 GATGGCCATAATGGAACATTCTTACTATGGATCATTTGGATATCATGTTACAAACTTTTT
 841 TGCTGTGAGCAATAGATATGGAAACCCGGAGGACCTAAAGTATCTGATAGATAAAGCACA
 901 TAGCTTGGGTTTACAGGTTCTGGTGGATGTAGTTCACAGTCATGCAAGCAATAATGTCAC
 961 TGATGGCCTCAATGGCTTTGATATTGGCCAAGGTTCTCAAGAATCCTACTTTCATGCTGG
1021 AGAGCGAGGGTACCATAAGTTGTGGGATAGCAGGCTGTTCAACTATGCCAATTGGGAGGT
1081 TCTTCGTTTCCTTCTTTCCAACTTGAGGTGGTGGCTAGAAGAGTATAACTTTGACGGATT
1141 TCGATTTGATGGAATAACTTCTATGCTGTATGTTCATCATGGAATCAATATGGGATTTAC
1201 AGGAAACTATAATGAGTATTTCAGCGAGGCTACAGATGTTGATGCTGTGGTCTATTTAAT
1261 GTTGGCCAATAATCTGATTCACAAGATTTTCCCAGACGCAACTGTTATTGCCGAAGATGT
1321 TTCTGGTATGCCGGGCCTTAGCCGGCCTGTTTCTGAGGGAGGAATTGGTTTTGATTACCG
1381 CCTGGCAATGGCAATCCCAGATAAGTGGATAGATTATTTAAAGAATAAGAATGATGAAGA
1441 TTGGTCCATGAAGGAAGTAACATCGAGTTTGACAAATAGGAGATATACAGAGAAGTGTAT
1501 AGCATATGCGGAGAGCCATGATCAGTCTATTGTCGGTGACAAGACCATTGCATTTCTCCT
```

```
-continued

1561 AATGAACAAAGAGATGTATTCTGGCATGTCTTGCTTGACAGATGCTTCTCCTGTTGTTGA

1621 TGCAGGAATTGCGCTTGACAAGATGATCCATTTTTTTCACAATGGCCTTGGGAGGAGAGG

1681 GGTACCTCAATTTCATGGGTAACGAGTTTGGCCATCCTGAGTGGATTGACTTCCCTAGTG

1741 AGGGCAATAATTGGAGTTATGACAAATGTAGACGCCAGTGGAACCTCGCAGATAGCGAAC

1801 ACTTGAGATACAAGTTTATGAATGCATTTGATAGAGCTATGAATTCGCTCGATGAAAAGT

1861 TCTCATTCCTCGCATCAGGAAAACAGATAGTAAGCAGCATGGATGATGATAATAAGGTTG

1921 TTGTGTTTGAACGTGGTGACCTGGTATTTGTATTCAACTTCCACCCAAATAACACATACG

1981 AAGGGTATAAAGTTGGATGTGACTTGCCAGGGAAGTACAGAGTTGCACTGGACAGTGATG

2041 CTTGGGAATTTGGTGGCCATGGAAGAGCTGGTCATGATGTTGACCATTTCACATCACCAG

2101 AAGGAATACCTGGAGTTCCAGAAACAAATTTCAATGGTCGTCCAAATTCCTTCAAAGTGC

2161 TGTCTCCTGCGCGAACATGTGTGGCTTATTACAGAGTTGATGAACGCATGTCATAAACTG

2221 AAGATTACCAGACAGACATTTGTAGTGAGCTACTACCAACAGCCAATATCGAGGAAAGTG

2281 ACGAGAAACTTAAAGATTCATCATCTACAAATATCAGTACATCATCTACAAAAAATGCTT

2341 ATTACAGAGTTGATGAACGCATGTCAGAAGCTGAAGATTACCAGACAGACATTTGTAGTG

2401 AGCTACTACTACCAACAGCCAATATCGAGGAGAGTGACGAGAAACTTGATGATTCATTAT

2461 CTACAAATATCAGTAACATTGGTCAGACTGTTGTAGTTTCTGTTGAGGAGAGAGACAAGG

2521 AACTTAAAGATTCACCATCTGTAAGCATCATTAGTGATGCTGTTCCAGCTGAATGGGCTG

2581 ATTCGGATGCAAACGTCTGGGGTGAGGACTAGTCAGATGATTGATCGATCCTTCTACGTT

2641 GGTGATCTCGGTCCGTGCATGATGTCTTCAGGGTGGTAGCATTGACTGATTGCATCATAG

2701 TTTTTTTTTTTTTTTTAAGTATTTCCTCTATGCATATTATTAGCATCCAATAAATTTAC

2761 TGGTTGTTGTACATAGAAAAAGTGCATTTGCATGTATGTGTTTCTCTGAAATTTTCCCCA

2821 GTTTTGGTGCTTTGCCTTTGGAGCCAAGTCTCTATATGTAATAAGAAAACTAAGAACAAT

2881 CACATATATAAAATGTTAGTAGATTACCA
``` or a fragment or modified sequence thereof, which upon expression a plant leads to the formation of a protein participating in formation of α-1,6 linkages of glucose monomers.

2. Plasmid p35 S-BE (DSM 6143).
3. Plasmid p35 S-anti-BE (DSM 6144).
4. Plasmid pB33-BE (DSM 6145).
5. Plasmid pB33-anti-BE (DSM 6146).
6. An isolated DNA sequence encoding potato branching enzyme, wherein said enzyme participates in the formation of α-1,6 linkages of glucose monomers.
7. A process for the production of a transgenic potato plant with an increased degree of branching of amylopectin starch relative to a non-transformed plant, comprising the following steps:
   a) production of a DNA molecule comprising the following sequences:
      i) a promoter which is active in the plant and ensures the formation of RNA in proposed target tissues or target cells,
      ii) a structural DNA sequence comprising the sequence identified as SEQ ID No. 1, which allows the transcription of an RNA which in the transgenic plant codes for a new protein sequence with the enzymatic activity of a branching enzyme, wherein said enzyme participates in the formation of α-1,6 linkages of glucose monomers;
   b) transfer and incorporation of the DNA sequence into the genome of a potato plant cell using recombinant plasmids; and
   c) regeneration of an intact, whole potato plant from the transformed potato plant cell.
8. The method according to claim 7, wherein the DNA molecule further comprises a 3'-non-translated sequence which in plant cells leads to termination of transcription and to the addition of a poly-A tail to the 3'-end of the RNA.
9. A process for the production of a transgenic potato plant with a reduced degree of branching of amylopectin starch relative to a non-transformed plant, comprising the following steps:
   a) production of a DNA molecule comprising the following sequences:
      i) a promoter which is active in the plant and ensures the formation of RNA in proposed target tissues or target cells,
      ii) a structural DNA sequence comprising the sequence identified as SEQ ID No. 1, which allows the transcription of an RNA which in the transgenic plant prevents the synthesis of a protein with the enzymatic activity of a branching enzyme, wherein said enzyme participates in the formation of α-1,6 linkages of glucose monomers;
   b) transfer and incorporation of the DNA sequence into the genome of a potato plant cell using recombinant plasmids; and c) regeneration of an intact, whole potato plant from the transformed potato plant cell.

10. The method according to claim 9, wherein the DNA molecule further comprises a 3'-non-translated sequence which in plant cells leads to termination of transcription and to the addition of a poly-A tail to the 3'-end of the RNA.

11. A transgenic plant produced via the process according to claims 7 or 9, wherein said promoter is heterologous and said promoter is operably linked to said structural DNA sequence.

12. The transgenic plant according to claim 11, wherein the plant is a commercially useful plant that produces phytoglycogen.

13. The transgenic plant according to claim 12, wherein the commercially useful plant is selected from the group consisting of maize, barley, wheat, rice, pea, soya bean, sugar cane, sugar beet, tomato, potato and tobacco.

14. A method for the production of transgenic potato plants in which the number of α-1,6 linkages of glucose monomers within phytoglycogen molecules is reduced relative to a non-transformed plant, using the plasmids according to claims 5 or 3.

15. A method for the production of transgenic plants according to claim 14, wherein the plants are commercially used plants selected from the group consisting of maize, barley, wheat, rice, pea, soya bean, sugar cane, sugar beet, tomato, potato and tobacco.

16. A recombinant expression vector comprising a DNA sequence encoding a plant branching enzyme from potato, wherein said enzyme participates in the formation of α-1,6 linkages of glucose monomers, wherein the vector is capable of expressing plant branching enzyme in a transformed plant cell or transgenic plant, or comprising a DNA sequence which allows the expression of an antisense RNA that leads to the inhibition of formation of a protein which displays the activity of branching enzyme in a transformed potato plant cell or transgenic potato plant.

17. The recombinant expression vector of claim 16, wherein the DNA sequence encoding plant branching enzyme comprises the DNA sequence identified as SEQ ID NO:1, or a fragment or modified sequence thereof, which upon expression leads to the formation of a protein participating in the formation of α-1,6 linkages of glucose monomers.

18. A potato plant cell or plant transformed with the vector of claim 16, wherein the plant cell or plant is capable of expressing an increased amount of a plant branching enzyme participating in the formation of α-1,6 linkages of glucose monomers relative to a non-transformed plant, or wherein the expression of said branching enzyme is inhibited.

19. The potato plant cell or plant according to claim 18, wherein the DNA sequence encoding plant branching enzyme, comprises the DNA sequence identified as SEQ ID NO:1, or a fragment or modified sequence thereof, which upon expression leads to the formation of a protein participating in the formation of α-1,6 linkages of glucose monomers, or wherein the expression of an antisense RNA leads to the inhibition of formation of protein participating in the formation of α-1,6 linkages of glucose monomers.

20. A composition comprising nucleic acid molecules comprising isolated sequences which are complementary to the sequences according to claim 1.

21. A composition comprising nucleic acid molecules comprising fragments of the isolated sequences according to claims 1 or 20, wherein said fragments of the sequences are able to selectively hybridize to the sequences, and wherein said fragments display the activity of a branching enzyme which participates in the formation of α-1.6 linkages of glucose monomers.

* * * * *